(12) United States Patent
Subasic

(10) Patent No.: US 11,974,720 B2
(45) Date of Patent: May 7, 2024

(54) MEDICAL DEVICE ACCESSORY MOUNTING SYSTEM

(71) Applicant: BOSTON SCIENTIFIC SCIMED, INC., Maple Grove, MN (US)

(72) Inventor: John Subasic, Boston, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 158 days.

(21) Appl. No.: 17/371,252

(22) Filed: Jul. 9, 2021

(65) Prior Publication Data

US 2022/0015611 A1 Jan. 20, 2022

Related U.S. Application Data

(60) Provisional application No. 63/051,996, filed on Jul. 15, 2020.

(51) Int. Cl.
*A61B 1/00* (2006.01)
(52) U.S. Cl.
CPC ...... *A61B 1/00131* (2013.01); *A61B 1/00066* (2013.01); *A61B 1/00121* (2013.01)
(58) Field of Classification Search
CPC ............ A61B 1/00066; A61B 1/00121; A61B 1/00128; A61B 1/00131; A61B 1/00112
See application file for complete search history.

(56) References Cited

U.S. PATENT DOCUMENTS

| | | | |
|---|---|---|---|
| 5,431,150 A * | 7/1995 | Yabe | A61B 46/10 600/157 |
| 5,514,074 A * | 5/1996 | Yabe | A61B 1/0051 600/123 |
| 5,695,491 A | 12/1997 | Silverstein | |
| 6,893,393 B2 | 5/2005 | Carrillo | |
| 7,223,230 B2 | 5/2007 | Zirps et al. | |
| 7,615,004 B2 | 11/2009 | Stokes et al. | |
| 7,803,107 B2 | 9/2010 | Carrillo | |
| 8,007,432 B2 | 8/2011 | Vakharia et al. | |
| 8,734,327 B2 | 5/2014 | Dillon | |
| 9,254,077 B2 | 2/2016 | Soetermans | |
| 9,486,125 B2 | 11/2016 | James | |
| 9,723,973 B2 | 8/2017 | Dillon et al. | |
| 2015/0164307 A1 | 6/2015 | Galperin et al. | |
| 2016/0089008 A1 | 3/2016 | Simmons | |
| 2017/0188796 A1* | 7/2017 | Olden | A61B 1/00135 |
| 2018/0361055 A1 | 12/2018 | Pereira et al. | |

* cited by examiner

*Primary Examiner* — Aaron B Fairchild
(74) *Attorney, Agent, or Firm* — Seager, Tufte & Wickhem, LLP

(57) ABSTRACT

A medical accessory mounting system may include a medical device having a handle and an elongate shaft extending distally from the handle. The handle may include at least one connecting structure formed in an outer surface of the handle, the at least one connecting structure comprising a plurality of ridges. The at least one connecting structure may be configured to engage with an accessory connecting structure formed on an outer surface of an accessory device.

18 Claims, 13 Drawing Sheets

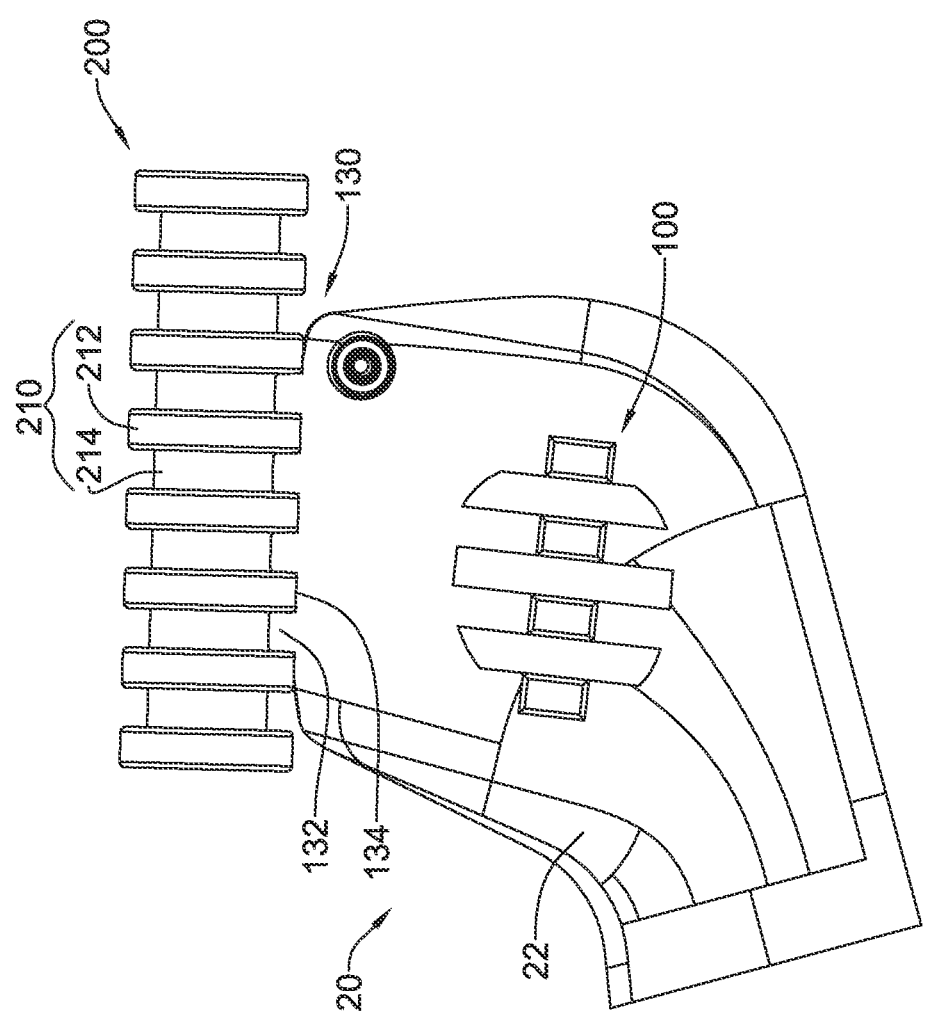

MEDICAL DEVICE ACCESSORY MOUNTING SYSTEM

CROSS REFERENCE TO RELATED APPLICATIONS

This application claims the benefit of and priority to U.S. Provisional Patent Application Ser. No. 63/051,996 filed on Jul. 15, 2020, the disclosure of which is incorporated herein by reference.

TECHNICAL FIELD

The disclosure is directed to a medical device system. More particularly, the disclosure is directed to an accessory mounting system for medical devices.

BACKGROUND

Various accessory devices may be used with an endoscopic device to perform various diagnostic and treatment procedures in the imaged cavity. For example, flexible ureteroscopy (fURS), gynecology, and other endoscopic procedures may require multiple medical devices and/or accessories. However, the accessory devices may not always be compatible with the endoscopic device. For example, the physical configurations of the devices may be difficult to use in conjunction. Mechanical connectivity between devices used together may facilitate smoother procedures. Of the known medical devices, systems, and methods, each has certain advantages and disadvantages. There is an ongoing need to provide alternative medical devices and fluid delivery systems.

SUMMARY

In one example, a medical accessory mounting system may comprise a medical device having a handle and an elongate shaft extending distally from the handle. The handle may include at least one connecting structure formed in an outer surface of the handle, the at least one connecting structure comprising a plurality of ridges. The at least one connecting structure may be configured to engage with an accessory connecting structure formed on an outer surface of an accessory device.

In addition or alternatively to any example described herein, the at least one connecting structure further comprises a plurality of valleys, each valley being disposed between adjacent ridges of the plurality of ridges.

In addition or alternatively to any example described herein, the plurality of ridges are oriented parallel to each other.

In addition or alternatively to any example described herein, the accessory connecting structure is releasably engageable with the at least one connecting structure without the use of fasteners.

In addition or alternatively to any example described herein, the accessory connecting structure is releasably engageable with the at least one connecting structure without the use of latches.

In addition or alternatively to any example described herein, the accessory connecting structure is releasably engageable with the at least one connecting structure without the use of tools.

In addition or alternatively to any example described herein, the at least one connecting structure includes a first connecting structure and a second connecting structure.

In addition or alternatively to any example described herein, the accessory connecting structure is engageable with the first connecting structure and the second connecting structure.

In addition or alternatively to any example described herein, the accessory connecting structure comprises a plurality of ridges and a plurality of valleys.

In addition or alternatively to any example described herein, a medical accessory mounting system may comprise a medical device having a handle and an elongate shaft extending distally from the handle. The handle may include at least one connecting structure formed in an outer surface of the handle, the at least one connecting structure includes a first connecting structure comprising a first plurality of ridges oriented parallel to each other and a second connecting structure comprising a second plurality of ridges oriented parallel to each other. The at least one connecting structure may be configured to engage with an accessory connecting structure comprising a plurality of ridges oriented parallel to each other formed on an outer surface of an accessory device.

In addition or alternatively to any example described herein, the at least one connecting structure is monolithically formed with the outer surface of the handle.

In addition or alternatively to any example described herein, the accessory connecting structure is monolithically formed with the outer surface of the accessory device.

In addition or alternatively to any example described herein, the first plurality of ridges are oriented transverse to a longitudinal axis of the handle.

In addition or alternatively to any example described herein, the second plurality of ridges are oriented transverse to a longitudinal axis of the handle.

In addition or alternatively to any example described herein, an endoscopic system may comprise an endoscope having a handle and an elongate shaft extending distally from the handle; and an endoscopic accessory device. The handle may include at least one connecting structure formed in an outer surface of the handle, the at least one connecting structure comprising a plurality of ridges. The at least one connecting structure may be configured to engage with an accessory connecting structure formed on an outer surface of the endoscopic accessory device.

In addition or alternatively to any example described herein, the at least one connecting structure includes a first connecting structure and a second connecting structure spaced apart from the first connecting structure.

In addition or alternatively to any example described herein, the at least one connecting structure includes a third connecting structure spaced apart from the first connecting structure and the second connecting structure.

In addition or alternatively to any example described herein, the accessory connecting structure is engageable with the at least one connecting structure using a male-to-male engagement.

In addition or alternatively to any example described herein, the at least one connecting structure includes a plurality of ridges and a plurality of valleys, wherein the plurality of ridges are oriented transverse to a longitudinal axis of the handle.

In addition or alternatively to any example described herein, adjacent ridges of the plurality of ridges are spaced apart from each other by one of the plurality of valleys, each of the ridges and valleys being oriented parallel to each other.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The invention may be more completely understood in consideration of the following detailed description in connection with the accompanying drawings, in which:

FIGS. 9A-9B illustrate engagement of the accessory device of FIG. 6 with the medical device of FIGS. 1-5;

Figure 1:
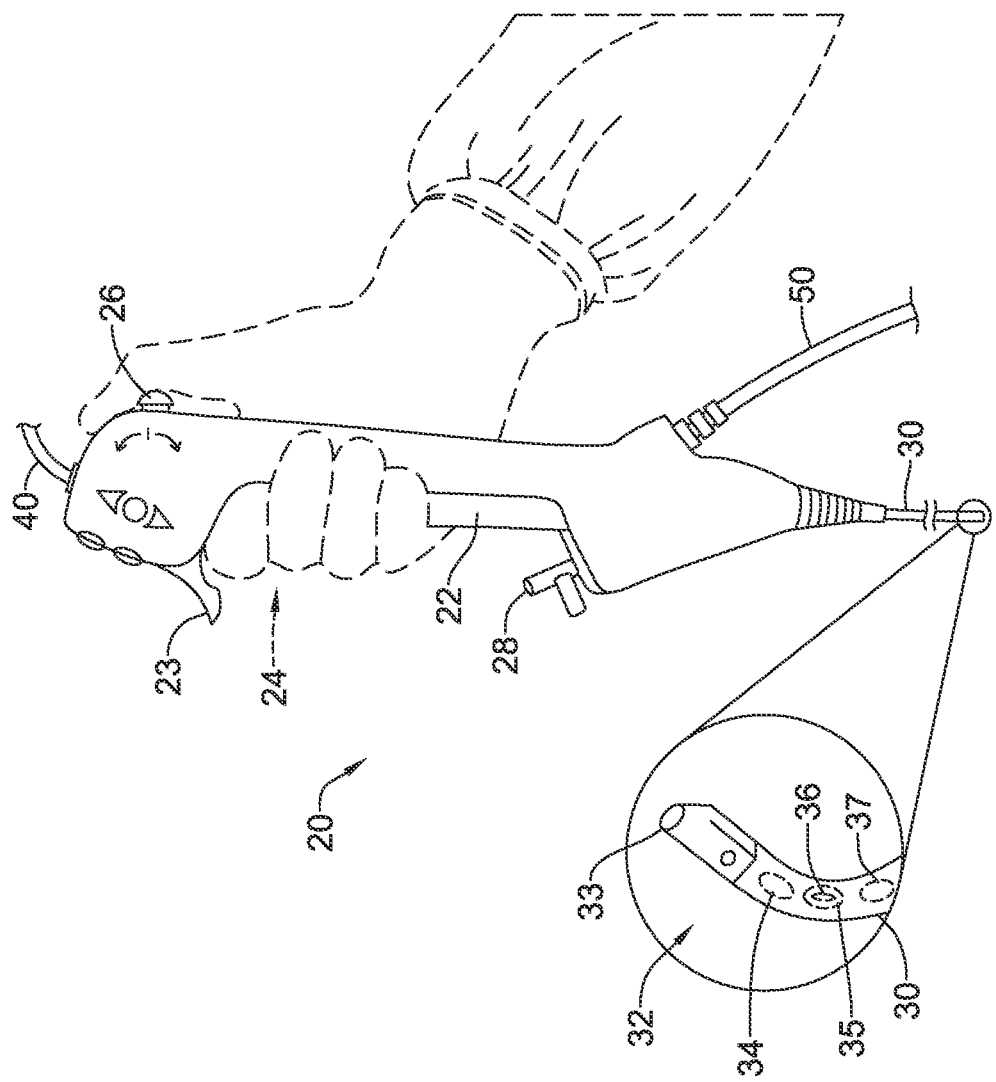
FIG. 1 illustrates a medical device manipulatable by medical personnel.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "extent" and/or "maximum extent" may be understood to mean a greatest measurement of a stated or identified dimension, while the term "minimum extent" may be understood to mean a smallest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" or "maximum extent" may be considered a greatest possible dimension measured according to the intended usage. Alternatively, a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Figure 2:
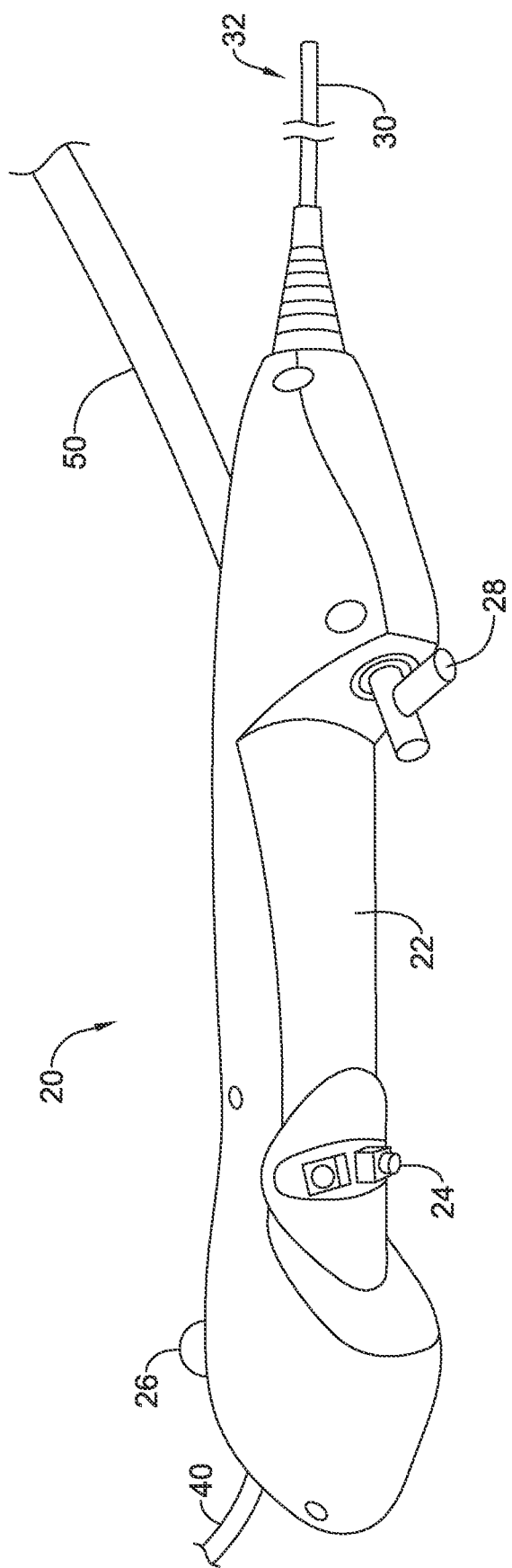
FIG. 2 is a perspective view illustrating selected aspects of the medical device of FIG. 1.

FIGS. 1-2 illustrate aspects of a medical device 20 (e.g., an endoscope, etc.) that may be used in conjunction with a fluid management system (not shown). In some embodiments, the medical device 20 may be a ureteroscope such as a LithoVue' scope. However, other medical devices, such as another endoscope, may be used in addition to or in place of a ureteroscope. The medical device 20 may include a handle 22 and an elongate shaft 30 extending distally from the handle 22. The medical device 20 may be configured to deliver fluid from the fluid management system to a treatment site via the elongate shaft 30, which may be configured to access the treatment site within the patient. In some embodiments, an inflow pump may be in fluid communication with the medical device 20 and/or the elongate shaft 30. The elongate shaft 30 may include one or more working lumens for receiving a flow of fluid or other medical devices therethrough. The medical device 20 is connected to the fluid management system via one or more supply line(s) 40.

In some embodiments, the medical device 20 may be in electronic communication with a workstation via a wired connection 50. In some embodiments, the workstation may include a touch panel computer, an interface box for receiving the wired connection 50, a cart, and a power supply, among other features. Other configurations are also contemplated. In some embodiments, the interface box may be configured with a wired or wireless communication connection with a controller of the fluid management system. The touch panel computer may include at least a display screen and an image processor. In some embodiments, the workstation may be a multi-use component (e.g., used for more than one procedure) while the medical device 20 may be a single use device, although this is not required. In some embodiments, the workstation may be omitted and the medical device 20 may be electronically coupled directly to the controller of the fluid management system.

In some embodiments, the one or more supply line(s) 40 from the fluid management system to the medical device 20 may be formed of a material the helps dampen the peristaltic motion created by the inflow pump. In some embodiments, the supply line(s) 40 may formed from small diameter tubing less than or equal to 1/16 inches (1.5875 millimeters) in diameter. However, it will be understood that tubing size may vary based on the application. The supply line(s) 40 and/or the tubing may be disposable and provided sterile and ready to use. Different types of tubing may be used for various functions within the fluid management system. For example, one type of tubing may be used for fluid heating and fluid flow control to the medical device 20 while another type of tubing may be used for irrigation within the body and/or the treatment site.

As seen in FIG. 1, the medical device 20 may include one or more sensors proximate a distal end 32 of the elongate shaft 30. For example, the medical device 20 may include a pressure sensor 34 at a distal tip of the elongate shaft 30 to measure intracavity pressure within the treatment site. The medical device 20 may also include other sensors such as, for example, a temperature sensor 35, a Fiber Bragg grating optical fiber 37 to detect stresses, and/or an antenna or electromagnetic sensor 36 (e.g., a position sensor). In an illustrative embodiment, the distal end 32 of the elongate shaft 30 and/or the medical device 20 may also include at least one camera 33 to provide a visual feed to the user on a display screen. In another embodiment, the at least one camera 33 may include two cameras having different communications requirements or protocols so that different information may be relayed to the user by each camera. When so provided, the user may switch back and forth between cameras at will through a touch screen interface and/or a touch panel computer. While not explicitly shown, the elongate shaft 30 may include one or more working lumens for receiving the fluid and/or other medical devices.

In some embodiments, the location of the distal end 32 of the elongate shaft 30 may be tracked during use. For example, a mapping and navigation system may include an operating table (or other procedural or examination table or chair, etc.) configured to act or function as an electromagnetic generator to generate a magnetic field of a known geometry. In some embodiments, a position sensor (e.g., the electromagnetic sensor 36, etc.) or other antenna, may be incorporated into the distal end 32 of the elongate shaft 30 of the medical device 20. The position sensor may be configured for use in sensing a location of the position sensor in the magnetic field of the mapping and navigation system. In some embodiments, the position sensor may be electronically coupled to a workstation. When the position sensor is in the magnetic field, the location of the position sensor can be mathematically determined relative to the electromagnetic field source (e.g., the operating table and/or the electromagnetic generator). The workstation and/or control unit may communicate to determine the position of the position sensor relative to the patient.

The medical device 20 includes the handle 22 coupled to a proximal end of the elongate shaft 30. The handle 22 may have an optional fluid flow on/off switch 23, which allows the user to control when fluid is flowing through the medical device 20 and into the treatment site. The handle 22 may further include other buttons 24, 26 that perform other various functions. For example, in some embodiments, the handle 22 may include buttons to control the temperature of the fluid. It will be understood that while the exemplary embodiment describes a ureteroscope, the features detailed above may also be directly integrated into a cystoscope, an endoscope, a hysteroscope, or virtually any device with an image capability. In some embodiments, the medical device 20 may also include a drainage port 28 which may be connected to a drainage system (not shown). Some illustrative drainage systems are described in commonly assigned U.S. Patent Application Publication No. 2018/0361055, titled AUTOMATED FLUID MANAGEMENT SYSTEM, the disclosure of which is hereby incorporated by reference.

Briefly, the fluid management system may include an inflow pump configured to pump and/or transfer fluid from a fluid supply source (e.g., a fluid bag, etc.) to the medical device 20 and/or a treatment site within a patient at a fluid flow rate. In some cases, the fluid may pass through a fluid warming system for heating fluid to be delivered to the patient via the one or more supply line(s) 78 prior to entering the medical device 20. In some embodiments, the fluid management system may be one that may be used in an endoscopic procedure, such as flexible ureteroscopy (fURS) procedures (e.g., ureteroscopy, percutaneous nephrolithotomy (PCNL), benign prostatic hyperplasia (BPH), transurethral resection of the prostate (TURP), etc.), gynecology, and other endoscopic procedures. Some illustrative fluid warming systems are described in described in commonly assigned U.S. Patent Application Publication No. 2018/0361055, titled AUTOMATED FLUID MANAGEMENT SYSTEM, the entire disclosure of which is hereby incorporated by reference.

The flow of fluid, the pressure of the fluid, the temperature of the fluid, and/or other operational parameters may be controlled by or at least partially controlled by a controller. The controller may be in electronic communication (e.g., wired or wireless) with the medical device 20, the inflow pump, and/or the fluid warming system to provide control commands and/or to transfer or receive data therebetween. For example, the controller may receive data from the medical device 20 such as, but not limited to, pressure data and temperature data. The controller may then use the data received from the medical device 20 to control operational parameters of the inflow pump, the fluid warming system, and/or other features.

In some embodiments, the fluid management system may include a vacuum pump and a collection container in fluid communication with one or more collection drapes. In some embodiments, the vacuum pump may include a plurality of vacuum pumps. In some embodiments, the collection container may include a plurality of containers, canisters, and/or other receptacles, which may be fluidly connected to each other and/or the vacuum pump. The vacuum pump may be operatively and/or electronically connected to the controller. In some embodiments, the vacuum pump may be disposed adjacent to and/or near the collection container. Other configurations are also contemplated.

The fluid management system may also include one or more user interface components such as a touch screen interface. The touch screen interface includes a display and may include switches or knobs in addition to touch capabilities. In some embodiments, the controller may include the touch screen interface and/or the display. The touch screen interface allows the user to input/adjust various functions of the fluid management system such as, for example flow rate, pressure, or temperature. The user may also configure parameters and alarms (such as, but not limited to, an intracavity pressure limit, a system pressure limit, etc.), information to be displayed, and the procedure mode. It is contemplated that other systems configured to receive user input may be used in place of or in addition to the touch screen interface. In some embodiments, the fluid management system may also include further user interface components such as an optional foot pedal, a heater user interface, a fluid control interface, or other device to manually control various modular systems. For example, the optional foot pedal may be used to manually control flow rate. Some illustrative displays and other user interface components are described in described in commonly assigned U.S. Patent Application Publication No. 2018/0361055, titled AUTOMATED FLUID MANAGEMENT SYSTEM, the entire disclosure of which is hereby incorporated by reference.

The touch screen interface may be operatively connected to or may be a part of the controller. The controller may be a computer, tablet computer, or other processing device. The controller may be operatively connected to one or more system components such as, for example, the inflow pump, the fluid warming system, a fluid deficit management system, etc. In some embodiments, these features may be integrated into a single unit. The controller may be capable of and configured to perform various functions such as calculation, control, computation, display, etc. The controller may also be capable of tracking and storing data pertaining to the operations of the fluid management system and each component thereof. In an illustrative embodiment, the controller includes wired and/or wireless network communication capabilities, such as ethernet or Wi-Fi, through which the controller may be connected to, for example, a local area network. The controller may also receive signals from one or more of the sensors of the fluid management system. In some embodiments, the controller may communicate with databases for best practice suggestions and the maintenance of patient records which may be displayed to the user on the display.

In some embodiments, the fluid management system may include visual software or image recognition and analysis software. In some embodiments, the controller may be configured to include visual software/image recognition software that can detect visual noise based on variations in brightness (e.g., light monitoring), contrast, or color pixilation. If the image provided to the controller is determined to be not sufficiently clear or sharp, the fluid management system may temporarily increase the fluid flow rate or the fluid pressure to flush out debris from the treatment site to sharpen/clear the image. The fluid flow rate or the fluid pressure may be manually or automatically increased for a temporary time (e.g., a predetermined time period) or until the field of view is deemed to be sufficiently clear. This temporary increase ensures that the time at which the fluid flow rate or the fluid pressure is increased is limited to ensure that intracavity pressure does not exceed safe limits.

In some embodiments, the fluid management system may automatically adjust the fluid flow rate and/or the fluid pressure based on a measured intracavity temperature and/or a measured pressure, for example when the measured pressure reaches a preset pressure threshold. In some embodiments, the measured pressure may be an intracavity pressure measured within the treatment site, and the preset pressure threshold may be an intracavity pressure limit. The intracavity temperature and/or the intracavity pressure may be measured in situ using a temperature sensor 35 and/or a pressure sensor 34 mounted on the medical device 20 (e.g., FIG. 1) used in conjunction with the fluid management system. In some embodiments, the fluid management system may include pressure monitoring software so that the inflow pump may be configured by the user to be automatically started, stopped, and/or speed adjusted by the fluid management system to maintain a fluid pressure delivered to the treatment site at a target pressure and/or within a predetermined pressure range. For example, the pressure sensor 34 may detect intracavity pressure within the treatment site (for example, a kidney or uterus) and automatically alter the fluid flow rate and/or the fluid pressure within the fluid management system based on the measured intracavity (e.g., intrarenal or intrauterine) pressure. If the intracavity pressure is too high, the fluid management system may decrease the fluid flow rate and/or the fluid pressure and if the intracavity pressure is too low, the fluid management system may increase the fluid flow rate and/or the fluid pressure.

In some embodiments, the controller may be configured to calculate a fluid deficit representative of fluid lost, absorbed by the patient, and/or otherwise unaccounted for during a procedure. In some embodiments, the controller may be configured to notify a user when the total fluid deficit reaches a preset fluid deficit limit. In some embodiments, the controller may be configured to stop the inflow pump and/or the vacuum pump when the total fluid deficit reaches the preset fluid deficit limit. In some embodiments, the controller may be configured to notify a user when a total amount of fluid infused reaches a preset fluid infusion limit. In some embodiments, the controller may be configured to stop the inflow pump and/or the vacuum pump when the total amount of fluid infused reaches the preset fluid infusion limit.

Figure 3:
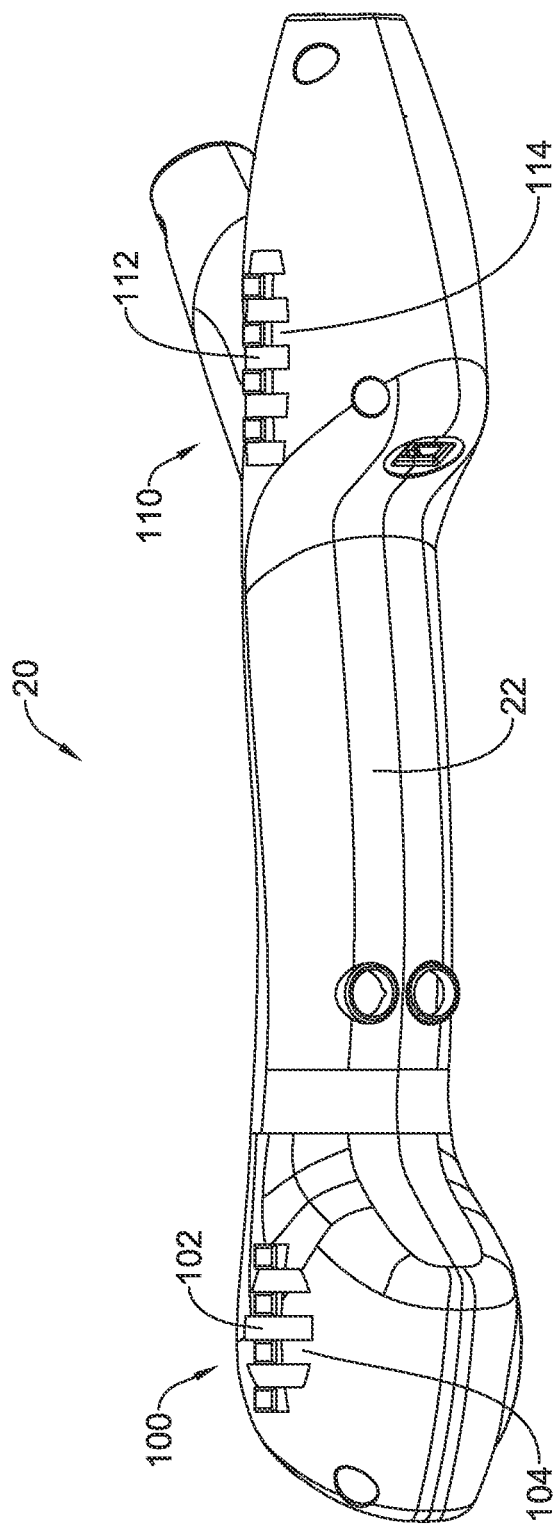
FIG. 3 is a perspective view illustrating aspects of a connecting feature provided with the medical device of FIG. 1.
Figure 4:
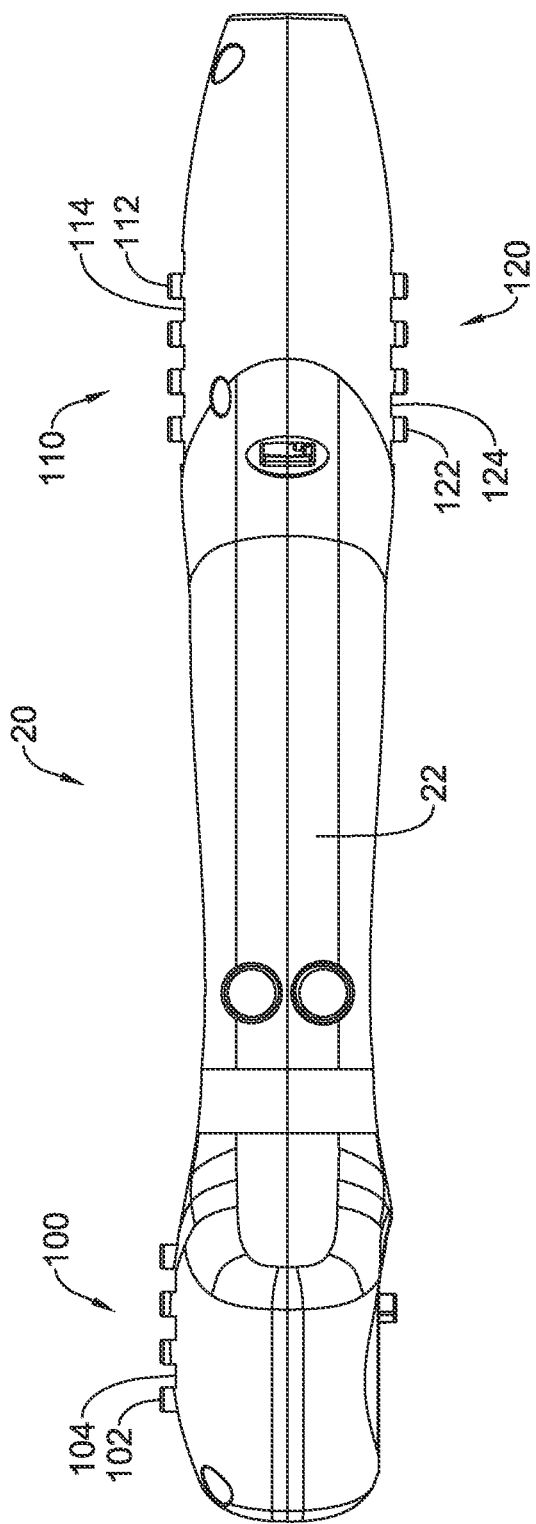
FIG. 4 is a side view illustrating aspects of the connecting feature shown in FIG. 3.
Figure 5:
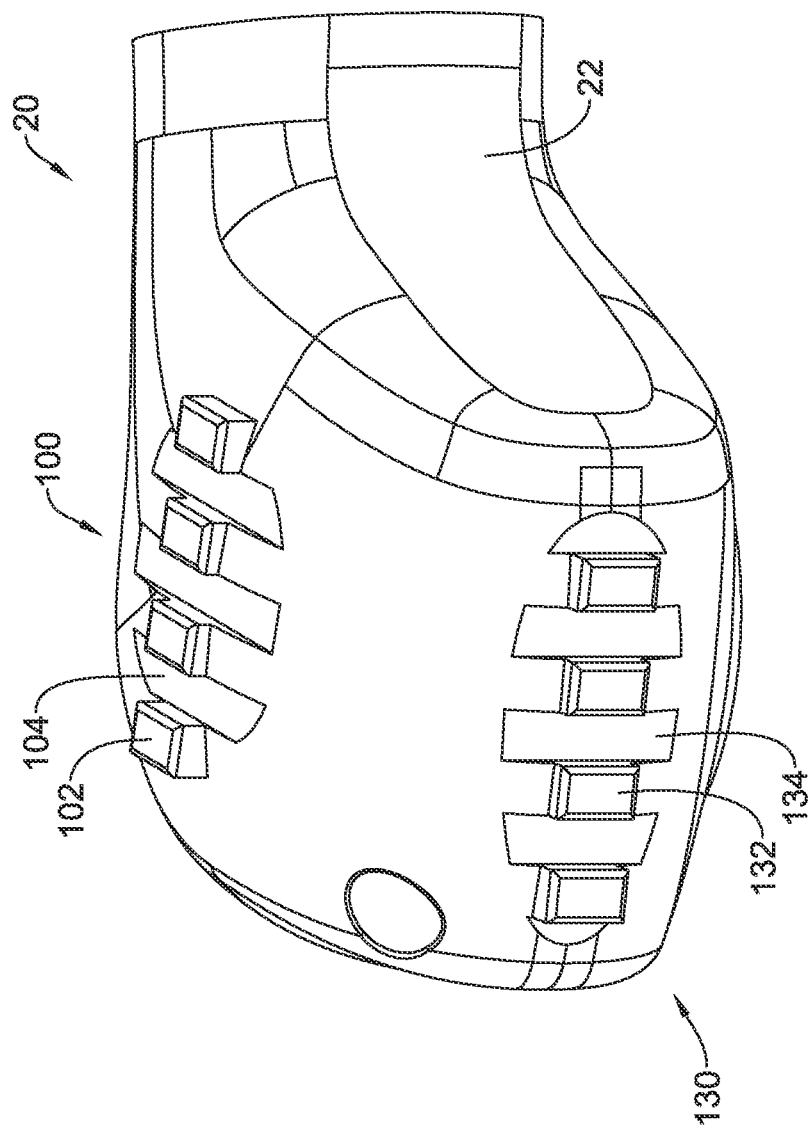
FIG. 5 is an enlarged view illustrating aspects of the connecting feature shown in FIG. 3.

In some embodiments, the medical device 20 (e.g., the endoscope, etc.) may be used in conjunction with one or more accessory devices to form a medical device system and/or an endoscopic system. In some embodiments, a medical accessory mounting system may include the medical device 20 having the handle 22 and the elongate shaft 30 extending distally from the handle 22. The handle 22 may include at least one connecting structure (e.g., ref. 100, 110, 120, 130) formed in an outer surface of the handle 22, as seen in FIGS. 3-5. In the interest of clarity, some features have been omitted from the handle 22 in FIGS. 3-5. The at least one connecting structure may include a plurality of ridges (e.g., ref 102, 112, 122, 132) and a plurality of valleys (e.g., ref. 104, 114, 124, 134), wherein each valley may be disposed between adjacent ridges of the plurality of ridges. Thus, the connecting structure may include a plurality of ridges alternating with valleys therebetween.

In some embodiments, the at least one connecting structure may be monolithically and/or integrally formed with the outer surface of the handle 22. In other words, the ridges and valleys of the connecting structure may be molded, etched, 3-D printed or otherwise formed during the formation of the handle. For instance, the ridges and valleys of the connecting structure may be molded during the same molding process in which the handle is formed, or the ridges and valleys of the connecting structure may be printed (e.g., 3-D printed) during the same printing process in which the handle is formed. In some embodiments, the plurality of ridges may be oriented substantially parallel to each other. In some embodiments, the plurality of ridges and/or the plurality of valleys may be oriented substantially transverse to a central longitudinal axis of the handle 22 and/or the elongate shaft 30. In some embodiments, adjacent ridges of the plurality of ridges may be spaced apart from each other by one of the plurality of valleys, each of the ridges and valleys being oriented substantially parallel to each other and/or substantially transverse to the central longitudinal axis of the handle 22 and/or the elongate shaft 30.

In some embodiments, the at least one connecting structure formed with the handle may include a first connecting structure 100, a second connecting structure 110, a third connecting structure 120, and/or a fourth connecting structure 130. In some embodiments, the medical device 20 and/or the handle 22 may include any one of the above referenced connecting structures and/or any combination thereof up to and including all of the above referenced connecting structures. The numerical nomenclature used herein is merely for identification purposes, and numerical nomenclature used in the claims may be considered to represent and/or correspond to a minimum number of the above referenced features that are present therein and not specifically to any particular connecting structure as designated by similar or in-common nomenclature.

As shown in FIG. 3 for example, the second connecting structure 110 may be spaced apart from the first connecting structure 100. In some embodiments, the first connecting structure 100 and the second connecting structure 110 may be disposed on a common side of the handle 22. For example, the first connecting structure 100 and the second connecting structure 110 may be formed in the outer surface of the handle 22 on one side of a plane extending through the handle 22 and having a central longitudinal axis of the handle 22 and/or the elongate shaft 30 disposed within the plane. In some embodiments, the first connecting structure 100 and/or the second connecting structure 110 may be monolithically and/or integrally formed with the outer surface of the handle 22.

The first connecting structure 100 may include a first plurality of ridges 102 and a first plurality of valleys 104. In at least some embodiments, the first plurality of ridges 102 and/or the first plurality of valleys 104 may be oriented substantially parallel to each other. In some embodiments, the first plurality of ridges 102 and/or the first plurality of valleys 104 may be oriented substantially transverse to the central longitudinal axis of the handle 22 and/or the elongate shaft 30. In some embodiments, adjacent ridges of the first plurality of ridges 102 may be spaced apart from each other by one of the first plurality of valleys 104, each of the ridges and valleys being oriented substantially parallel to each other and/or substantially transverse to the central longitudinal axis of the handle 22 and/or the elongate shaft 30. In some embodiments, the first plurality of ridges 102 may extend outward and/or away from the plane extending through the handle 22 and along the central longitudinal axis of the handle 22 and/or the elongate shaft 30 disposed within the plane. In some embodiments, the first plurality of ridges 102 may extend outward and/or away from the central longitudinal axis at a substantially perpendicular angle to the central longitudinal axis. In some embodiments, the first plurality of ridges 102 may extend outward and/or away from the plane at a substantially perpendicular angle to the plane.

The second connecting structure 110 may include a second plurality of ridges 112 and a second plurality of valleys 114. In at least some embodiments, the second plurality of ridges 112 and/or the second plurality of valleys 114 may be oriented substantially parallel to each other. In some embodiments, the second plurality of ridges 112 and/or the second plurality of valleys 114 may be oriented substantially transverse to the central longitudinal axis of the handle 22 and/or the elongate shaft 30. In some embodiments, adjacent ridges of the second plurality of ridges 112 may be spaced apart from each other by one of the second plurality of valleys 114, each of the ridges and valleys being oriented substantially parallel to each other and/or substantially transverse to the central longitudinal axis of the handle 22 and/or the elongate shaft 30. In some embodiments, the second plurality of ridges 122 may extend outward and/or away from the plane extending through the handle 22 and along the central longitudinal axis of the handle 22 and/or the elongate shaft 30 disposed within the plane. In some embodiments, the second plurality of ridges 112 may extend outward and/or away from the central longitudinal axis at a substantially perpendicular angle to the central longitudinal axis. In some embodiments, the second plurality of ridges 112 may extend outward and/or away from the plane at a substantially perpendicular angle to the plane.

FIG. 4 is a partially rotated view of the handle 22 of the medical device 20 of FIG. 3 illustrating that the at least one connecting structure may include a third connecting structure 120 spaced apart from the first connecting structure 100 and/or the second connecting structure 110. In some embodiments, the third connecting structure 120 may be disposed on an opposite side of the handle 22 from the first connecting structure 100 and the second connecting structure 110. For example, the first connecting structure 100 and the second connecting structure 110 may be formed in the outer surface of the handle 22 on one side of a plane extending through the handle 22 and having the central longitudinal axis of the handle 22 and/or the elongate shaft 30 disposed within the plane, and the third connecting structure 120 may be formed in the outer surface of the handle 22 on a second side and/or on an opposite side of the plane extending through the handle 22 and having the central longitudinal axis of the handle 22 and/or the elongate shaft 30 disposed within the plane. In some embodiments, the third connecting structure 120 may be monolithically and/or integrally formed with the outer surface of the handle 22.

The third connecting structure 120 may include a third plurality of ridges 122 and a third plurality of valleys 124. In at least some embodiments, the third plurality of ridges 122 and/or the third plurality of valleys 124 may be oriented substantially parallel to each other. In some embodiments, the third plurality of ridges 122 and/or the third plurality of valleys 124 may be oriented substantially transverse to the central longitudinal axis of the handle 22 and/or the elongate shaft 30. In some embodiments, adjacent ridges of the third plurality of ridges 122 may be spaced apart from each other by one of the third plurality of valleys 124, each of the ridges and valleys being oriented substantially parallel to each other and/or substantially transverse to the central longitudinal axis of the handle 22 and/or the elongate shaft 30. In some embodiments, the third plurality of ridges 122 may extend outward and/or away from the plane extending through the handle 22 and along the central longitudinal axis of the handle 22 and/or the elongate shaft 30 disposed within the plane. In some embodiments, the third plurality of ridges 122 may extend outward and/or away from the central longitudinal axis at a substantially perpendicular angle to the central longitudinal axis. In some embodiments, the third plurality of ridges 122 may extend outward and/or away from the plane at a substantially perpendicular angle to the plane.

FIG. 5 illustrates a portion of the handle 22 of the medical device 20, and further illustrates that the at least one connecting structure may include a fourth connecting structure 130 spaced apart from the first connecting structure 100, the second connecting structure 110, and/or the third connecting structure 120, as seen in FIG. 5. In some embodiments, the fourth connecting structure 130 may be disposed on a different side of the handle 22 from the first connecting structure 100, the second connecting structure 110, and/or the third connecting structure 120. For example, when compared to the first connecting structure 100, the second connecting structure 110, and/or the third connecting structure 120, the fourth connecting structure 130 may be formed in the outer surface of the handle 22 with the plane, referred to above as extending through the handle 22 and having the central longitudinal axis of the handle 22 and/or the elongate shaft 30 disposed within the plane, extending through and/or transecting the fourth connecting structure 130. In some embodiments, the side of the handle 22 having the fourth connecting structure 130 disposed therein may be oriented at a generally perpendicular angle to the sides having the first, second, and/or third connecting structures. For example, if the first connecting structure 100, the second connecting structure 110, and/or the third connecting structure 120 are considered to face towards the right and left sides of the handle 22, the fourth connecting structure 130 may be considered to face towards a top side or a bottom side of the handle 22. In some embodiments, the fourth connecting structure 130 may be monolithically and/or integrally formed with the outer surface of the handle 22.

The fourth connecting structure 130 may include a fourth plurality of ridges 132 and a fourth plurality of valleys 134. In at least some embodiments, the fourth plurality of ridges 132 and/or the fourth plurality of valleys 134 may be oriented substantially parallel to each other. In some embodiments, the fourth plurality of ridges 132 and/or the fourth plurality of valleys 134 may be oriented substantially transverse to the central longitudinal axis of the handle 22 and/or the elongate shaft 30. In some embodiments, adjacent ridges of the fourth plurality of ridges 132 may be spaced apart from each other by one of the fourth plurality of valleys 134, each of the ridges and valleys being oriented substantially parallel to each other and/or substantially transverse to the central longitudinal axis of the handle 22 and/or the elongate shaft 30. In some embodiments, the fourth plurality of ridges 132 may extend outward and/or away from the central longitudinal axis at a substantially perpendicular angle to the central longitudinal axis.

The ridges of the connecting structures may be defined by first and second side surfaces intersecting an outward facing surface. In some instances, the first and second side surfaces may extend parallel to one another, and be positioned at a perpendicular angle to the outward facing surface. In other instances, the first and second side surface may interest the outward facing surface at a non-perpendicular angle, such as an acute angle of about 70° to about 88°, about 75° to about 88°, about 80° to about 88°, about 70° to about 85°, about 75° to about 85°, or about 80° to about 85°, for example, or intersect at an obtuse angle of about 92° to about 110°, about 92° to about 105°, about 92° to about 100°, about 95° to about 110°, about 95° to about 105°, or about 95° to about 100°, for example. Thus, in some instances, the first and second side surfaces may converge toward one another as they extend toward the outward facing surface, or the first and second side surfaces may diverge away from one another as they extend toward the outward facing surface.

The valleys may define a base surface extending between a side surface of one ridge to a facing side surface of an adjacent ridge.

In some embodiments, an accessory device may include a motorized endoscopic deployment device for controlling an elongated end effector device to capture a target element (e.g., kidney stones or the like). The motorized deployment device may be compatible with the medical device 20 (e.g., the endoscope) or may be integrated with the medical device 20 in a monolithic handle. The elongated end effector device may refer to any one of a number of devices compatible with and actuated by the motorized deployment device. For example, the elongated end effector device may be a retrieval device for capturing kidney stones, a laser fiber device, a therapy needle, snares, forceps, band ligation devices, etc. Any of the elongated end effector devices may be fitted with, for example, a handle sized and shaped to be used with the motorized deployment device. Thus, any elongated end effector device compatible with and fitted with an appropriate handle (or a similar device) may also be used with the motorized deployment device. Other accessory devices are also contemplated.

Figure 6:
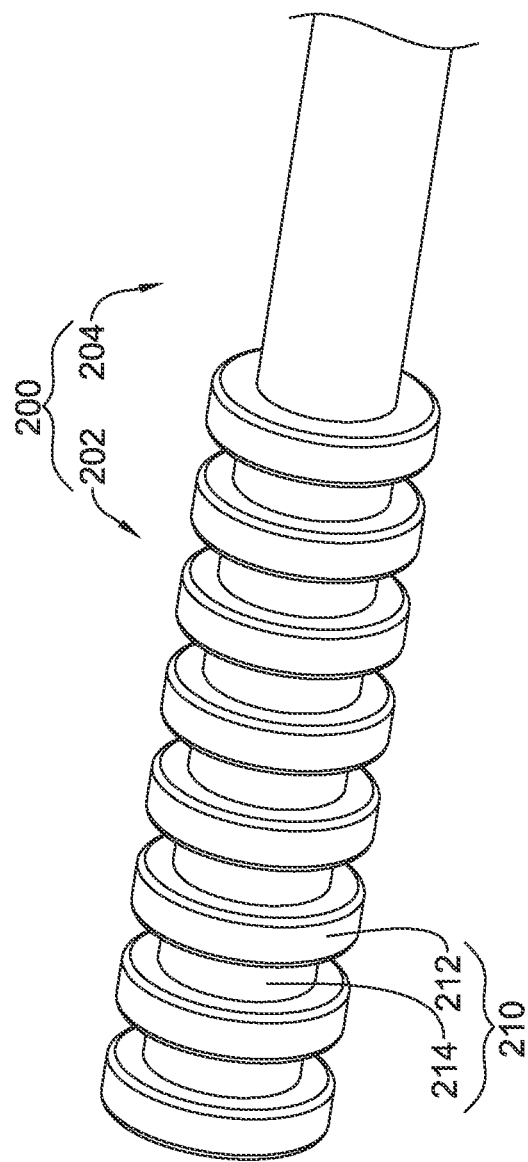
FIG. 6 is a perspective view illustrating selected aspects of an accessory device compatible with the medical device of FIGS. 1-5.
Figure 7:
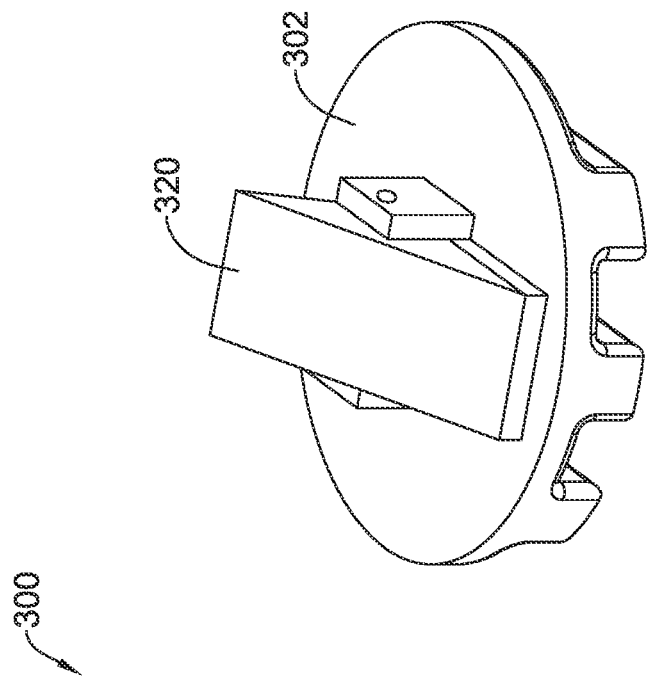
FIG. 7 illustrates selected aspects of an accessory device compatible with the medical device of FIGS. 1-5.
Figure 7:
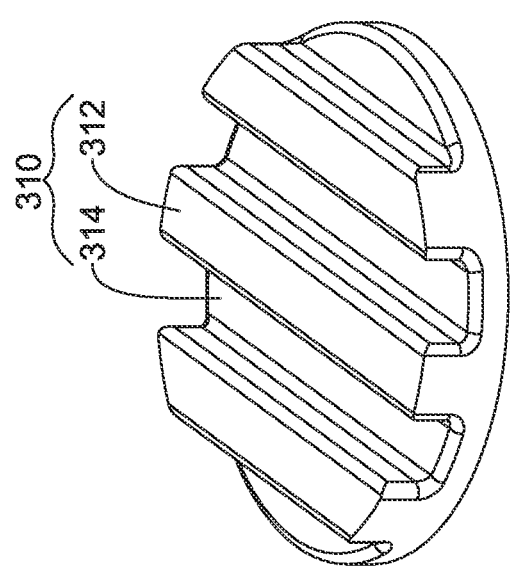
Figure 8:
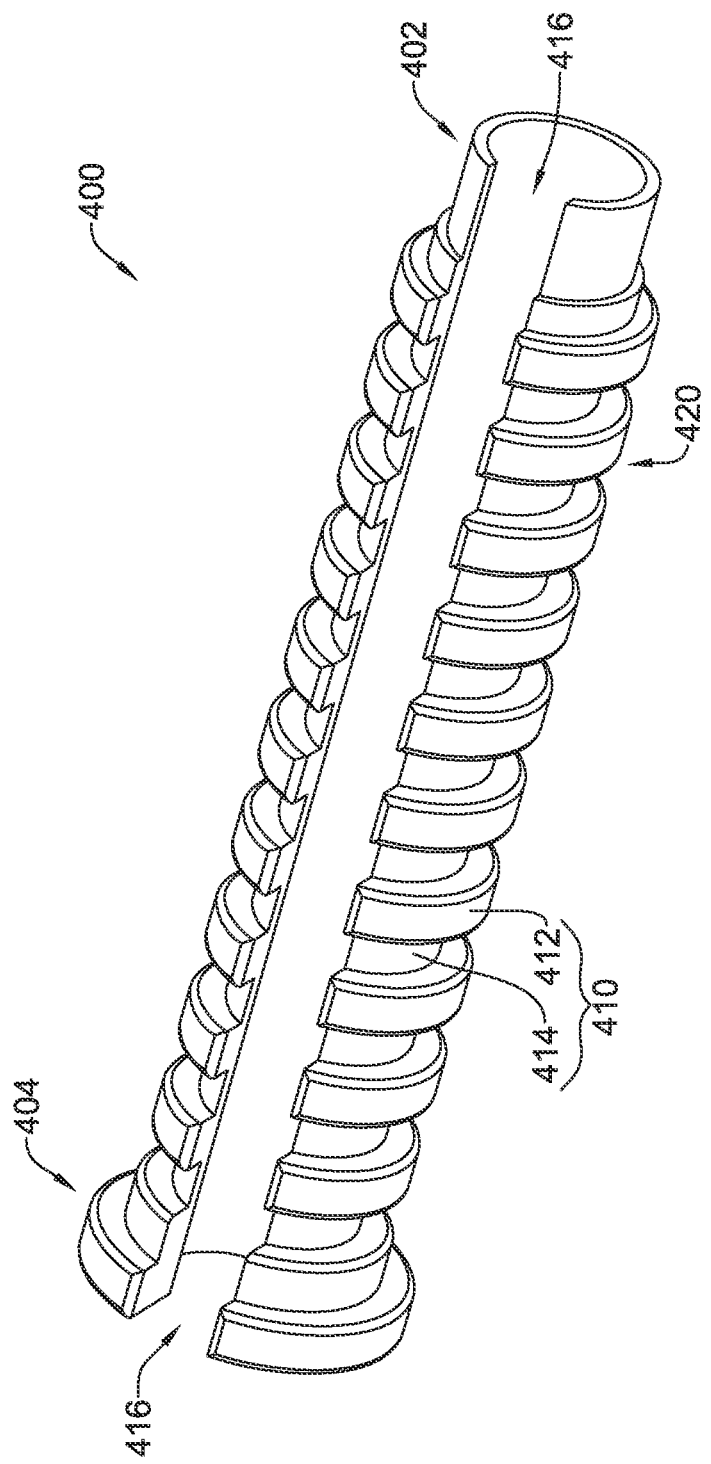
FIG. 8 illustrates selected aspects of an accessory device compatible with the medical device of FIGS. 1-5.

In some embodiments, the at least one connecting structure may be configured to engage with an accessory connecting structure (e.g., FIGS. 6-8, ref. 210, 310, 410) formed on an outer surface of an accessory device (e.g., FIGS. 6-8, ref. 200, 300, 400). In some embodiments, the accessory device described herein may include and/or may be an accessory device handle. In some embodiments, the accessory connecting structure may comprise a plurality of ridges (e.g., FIGS. 6-8, ref. 212, 312, 412) and a plurality of valleys (e.g., FIGS. 6-8, ref. 214, 314, 414), wherein each valley may be disposed between adjacent ridges of the plurality of ridges. In some embodiments, the plurality of ridges of the accessory connecting structure may be oriented substantially parallel to each other.

As with the connecting structure of the handle discussed above, the ridges of the accessory connecting structures of may be defined by first and second side surfaces intersecting an outward facing surface. In some instances, the first and second side surfaces may extend parallel to one another, and be positioned at a perpendicular angle to the outward facing surface. In other instances, the first and second side surface may interest the outward facing surface at a non-perpendicular angle, such as an acute angle of about 70° to about 88°, about 75° to about 88°, about 80° to about 88°, about 70° to about 85°, about 75° to about 85°, or about 80° to about 85°, for example, or intersect at an obtuse angle of about 92° to about 110°, about 92° to about 105°, about 92° to about 100°, about 95° to about 110°, about 95° to about 105°, or about 95° to about 100°, for example. Thus, in some instances, the first and second side surfaces may converge toward one another as they extend toward the outward facing surface, or the first and second side surfaces may diverge away from one another as they extend toward the outward facing surface. The valleys may define a base surface extending between a side surface of one ridge to a facing side surface of an adjacent ridge.

FIG. 6 illustrates a portion of an example accessory device 200. In some embodiments, the accessory device 200 may include an accessory device handle 202 and/or an end effector device 204. In some embodiments, an outer surface of the accessory device 200 and/or the accessory device handle 202 may include an accessory connecting structure 210 comprising a plurality of ridges 212 and a plurality of valleys 214, wherein each valley may be disposed between adjacent ridges of the plurality of ridges 212.

In at least some embodiments, the plurality of ridges 212 and/or the plurality of valleys 214 may be oriented substantially parallel to each other. In some embodiments, the plurality of ridges 212 and/or the plurality of valleys 214 may be oriented substantially transverse to a central longitudinal axis of the accessory device 200, the accessory device handle 202, and/or the end effector device 204. In some embodiments, adjacent ridges of the plurality of ridges 212 may be spaced apart from each other by one of the plurality of valleys 214, each of the ridges and valleys being oriented substantially parallel to each other and/or extending radially outward from the central longitudinal axis of the accessory device 200, the accessory device handle 202, and/or the end effector device 204. In some embodiments, the plurality of ridges 212 may extend radially outward and/or away from the central longitudinal axis of the accessory device 200, the accessory device handle 202, and/or the end effector device 204 at a substantially right angle to the central longitudinal axis of the accessory device 200, the accessory device handle 202, and/or the end effector device 204. In some embodiments, the plurality of ridges 212 may be monolithically and/or integrally formed with the outer surface of the accessory device 200 and/or the accessory device handle 202.

FIG. 7 illustrates a portion of an example accessory device 300. In some embodiments, the accessory device 300 may include a flattened body 302 including a multi-purpose clip 320 attached thereto. In some embodiments, the multi-purpose clip 320 may be hingedly and/or pivotably connected to the flattened body 302. In some embodiments, the multi-purpose clip 320 may be useful and/or beneficial for tool management (e.g., containing and/or holding a guidewire, an end effector device, etc.). In some embodiments, the accessory device 300 may have one or more features other than or in addition to the multi-purpose clip 320. Other configurations are also contemplated. In some embodiments, an outer surface of the accessory device 300 and/or the flattened body 302 may include an accessory connecting structure 310 comprising a plurality of ridges 312 and a plurality of valleys 314, wherein each valley may be disposed between adjacent ridges of the plurality of ridges 312.

In at least some embodiments, the plurality of ridges 312 and/or the plurality of valleys 314 may be oriented substantially parallel to each other. In some embodiments, adjacent ridges of the plurality of ridges 312 may be spaced apart from each other by one of the plurality of valleys 314, each of the ridges and valleys being oriented substantially parallel to each other and/or extending outward and/or away from the flattened body 302 of the accessory device 300. In some embodiments, the plurality of ridges 312 may extend in an opposite direction from and/or away from the multi-purpose clip 320 with respect to the flattened body 302. In some embodiments, the plurality of ridges 312 may extend radially outward and/or away from the flattened body 302 of the accessory device 300 at a substantially perpendicular angle to the flattened body 302 of the accessory device 300. In some embodiments, the plurality of ridges 312 may be monolithically and/or integrally formed with the outer surface of the accessory device 300 and/or the flattened body 302 of the accessory device 300.

FIG. 8 illustrates an example accessory device 400. In some embodiments, the accessory device 400 may include and/or may be an accessory device handle configured to receive an end effector device. In some embodiments, an outer surface of the accessory device 400 and/or the accessory device handle may include an accessory connecting structure 410 comprising a plurality of ridges 412 and a plurality of valleys 414, wherein each valley may be disposed between adjacent ridges of the plurality of ridges 412. In at least some embodiments, a body 420 of the accessory device 400 and/or the accessory device handle may include a longitudinally oriented slot 416 extending from a proximal end 402 of the accessory device 400 and/or the accessory device handle to a distal end 404 of the accessory device 400 and/or the accessory device handle. The longitudinally oriented slot 416 may be configured to receive an end effector device therein in a transverse direction relative to a central longitudinal axis of the accessory device 400 and/or the accessory device handle, thereby negating the need to feed the end effector device axially through the accessory device 400 and/or the accessory device handle. In one example, the accessory device 400 may be either of a Segura™ or a Dakota™ handle.

In at least some embodiments, the plurality of ridges 412 and/or the plurality of valleys 414 may be oriented substantially parallel to each other. In some embodiments, the plurality of ridges 412 and/or the plurality of valleys 414 may be oriented substantially transverse to a central longitudinal axis of the accessory device 400 and/or the accessory device handle. In some embodiments, adjacent ridges of the plurality of ridges 412 may be spaced apart from each other by one of the plurality of valleys 414, each of the ridges and valleys being oriented substantially parallel to each other and/or extending radially outward from the central longitudinal axis of the accessory device 400 and/or the accessory device handle. In some embodiments, the plurality of ridges 412 may extend radially outward and/or away from the central longitudinal axis of the accessory device 400 and/or the accessory device handle at a substantially perpendicular angle to the central longitudinal axis of the accessory device 400 and/or the accessory device handle. In some embodiments, the plurality of ridges 412 may be monolithically and/or integrally formed with the outer surface of the accessory device 400 and/or the accessory device handle.

In some embodiments, a slide may slide over the body 420 of the accessory device 400 and/or the accessory device handle. A male luer may be attached to a distal end of the slide, while a shaft (e.g., a pull wire) of the end effector device is held by a jaw vise including a plurality of jaws at the proximal end 402 of the accessory device 400 and/or the body 420. A cap 430 (e.g., FIG. 11) may force the plurality of jaws closed around the shaft of the end effector device as the cap 430 is screwed onto the body 420. The body 420 may have a through-lumen for the shaft of the elongated end effector device. The slide may move relative to the body 420 and the shaft of the end effector device. An outer sheath of the end effector device may be connected via a female luer to the male luer and extend to cover the end effector at the distal end of the end effector device. When the slide is moved distally it in turn moves the outer sheath distally over the end effector device to close the end effector device, and when the slide is moved proximally it in turn moves the outer sheath proximally to uncover the distal end of the end effector device, causing a self-opening, memory set end effector device to open. A stroke-limiter in the accessory device 400 and/or the accessory device handle may govern the travel of the slide relative to the end effector size.

Some examples of end effector devices compatible with the accessory device 400 and/or the accessory device handle may include a stone/particle retrieval basket for capturing objects at a distal end of the endoscopic shaft, a laser fiber device for fragmenting and/or cauterizing objects at the distal end of the endoscopic shaft, a therapy needle for puncturing and/or supplying medicament to a treatment site, a snare for capturing objects at the distal end of the endoscopic shaft, a forceps for capturing and/or grasping objects at the distal end of the endoscopic shaft, and a band ligation device. Other end effector devices are also contemplated.

Figure 9A:
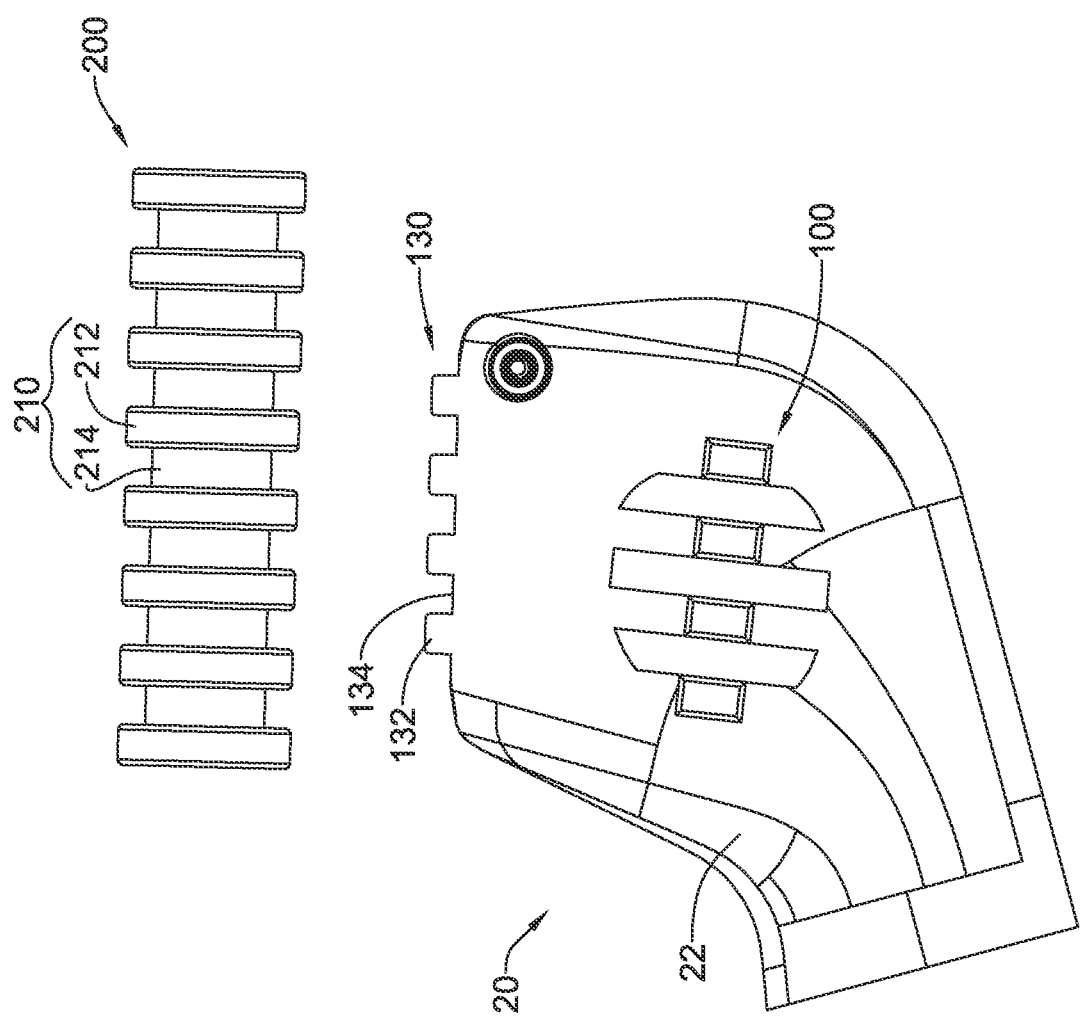

FIGS. 9A and 9B illustrate engagement of the accessory device 200 with a portion of the handle 22 of the medical device 20. As may be seen in the figures, the at least one connecting structure of the medical device 20 may be configured to engage with the accessory connecting structure 210 formed on the outer surface of the accessory device 200. Illustratively, FIGS. 9A and 9B illustrate engagement of the accessory device 200 with the fourth connecting structure 130 formed on the outer surface of the medical device 20 and/or the handle 22. As will be appreciated, the accessory device 200 and/or the accessory connecting structure 210 may be engageable with the first connecting structure 100, the second connecting structure 110 (not shown), the third connecting structure 120 (not shown), and/or the fourth connecting structure 130. In the interest of brevity, the accessory device 200 and/or the accessory connecting structure 210 is shown engaging the fourth connecting structure 130 of the handle 22 of the medical device 20 and is described accordingly.

In some embodiments, the at least one connecting structure of the medical device 20 may be configured to engage with the accessory connecting structure 210 via an interference fit, a press fit, a friction fit, and the like, as seen in FIG. 9B. Other means of engagement are also contemplated. The plurality of ridges 212 of the accessory connecting structure 210 may be configured to engage with and/or be received by the plurality of valleys (e.g., the fourth plurality of valleys 134) of the at least one connecting structure (e.g., the fourth connecting structure 130), and the plurality of ridges (e.g., the fourth plurality of ridges 132) of the at least one connecting structure (e.g., the fourth connecting structure 130) may be configured to engage with and/or be received by the plurality of valleys 214 of the accessory connecting structure 210. In some embodiments, the accessory connecting structure 210 may be engageable with the at least one connecting structure (e.g., the fourth connecting structure 130) using a male-to-male engagement. When the accessory connecting structure 210 is engaged with the connecting structure 130 of the handle 22 of the medical device 20, the side surfaces of the ridges 212 of the accessory connecting structure 210 may frictionally engage and press against the juxtaposed side surfaces of the ridges 132 of the connecting structure 130 of the handle 22.

In some embodiments, the accessory device 200 may be configured to be oriented with a central longitudinal axis substantially parallel to the central longitudinal axis of the medical device 20, the handle 22, and/or the elongate shaft 30 when the accessory connecting structure 210 is engaged with the at least one connecting structure (e.g., the first connecting structure 100, the second connecting structure 110, the third connecting structure 120, and/or the fourth connecting structure 130).

Additionally, in at least some embodiments, the accessory connecting structure 210 may be releasably engageable with the at least one connecting structure (e.g., the first connecting structure 100, the second connecting structure 110, the third connecting structure 120, and/or the fourth connecting structure 130) without the use of fasteners (e.g., screws, pins, clips, etc.). In some embodiments, the accessory connecting structure 210 may be releasably engageable with the at least one connecting structure (e.g., the first connecting structure 100, the second connecting structure 110, the third connecting structure 120, and/or the fourth connecting structure 130) without the use of latches. In some embodiments, the accessory connecting structure 210 may be releasably engageable with the at least one connecting structure (e.g., the first connecting structure 100, the second connecting structure 110, the third connecting structure 120, and/or the fourth connecting structure 130) without the use of tools.

Figure 10A:
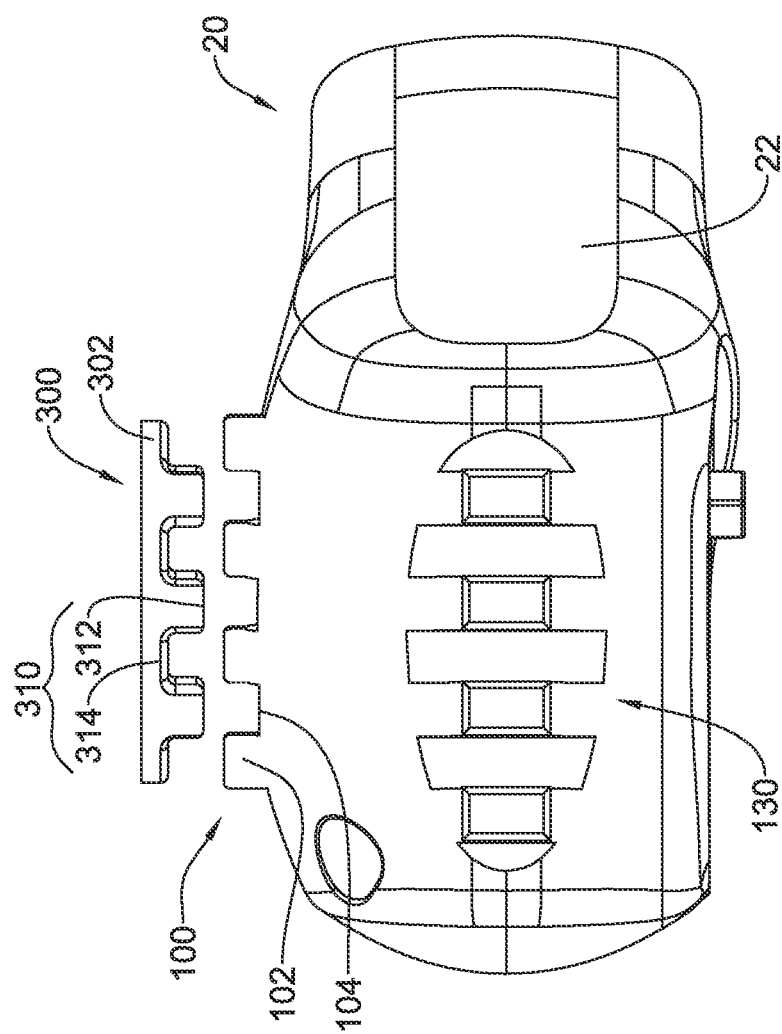
FIGS. 10A-10B illustrate engagement of the accessory device of FIG. 7 with the medical device of FIGS. 1-5.
Figure 10B:
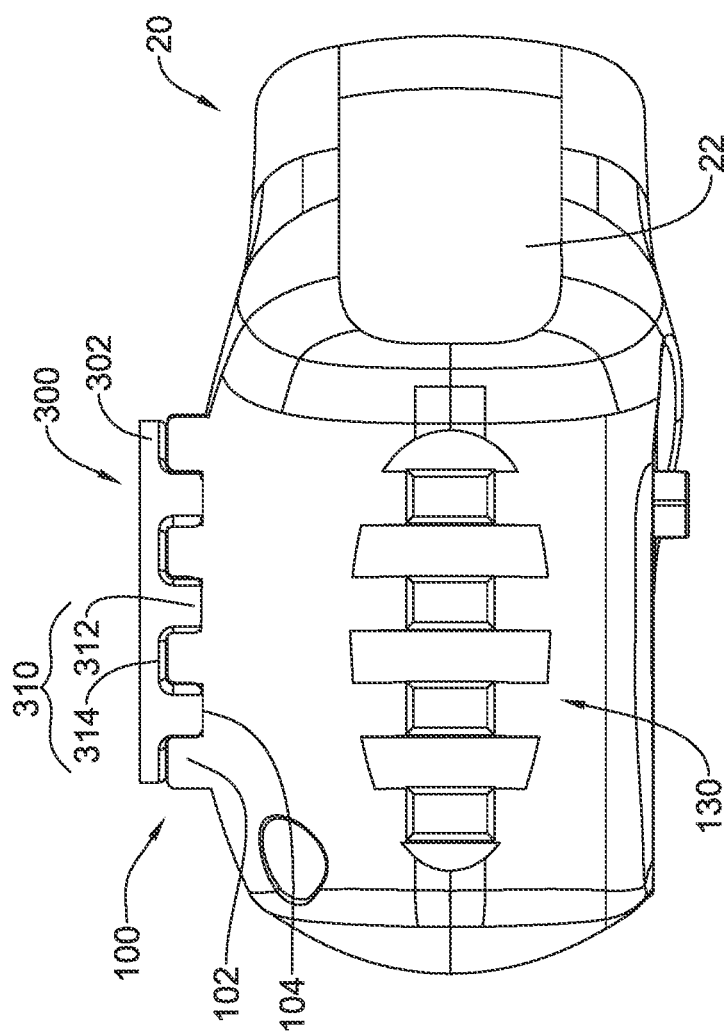

FIGS. 10A and 10B illustrate engagement of the accessory device 300 with a portion of the handle 22 of the medical device 20. Since it is not necessary to understand the engagement, the multi-purpose clip 320 has been omitted from FIGS. 10A and 10B. As may be seen in the figures, the at least one connecting structure of the medical device 20 may be configured to engage with the accessory connecting structure 310 formed on the outer surface of the accessory device 300. Illustratively, FIGS. 10A and 10B illustrate engagement of the accessory device 300 with the first connecting structure 100 formed on the outer surface of the medical device 20 and/or the handle 22. As will be appreciated, the accessory device 300 and/or the accessory connecting structure 310 may be engageable with the first connecting structure 100, the second connecting structure 110 (not shown), the third connecting structure 120 (not shown), and/or the fourth connecting structure 130. In the interest of brevity, the accessory device 300 and/or the accessory connecting structure 310 is shown engaging the first connecting structure 100 of the handle 22 of the medical device 20 and is described accordingly.

In some embodiments, the at least one connecting structure of the medical device 20 may be configured to engage with the accessory connecting structure 310 via an interference fit, a press fit, a friction fit, and the like, as seen in FIG. 10B. Other means of engagement are also contemplated. The plurality of ridges 312 of the accessory connecting structure 310 may be configured to engage with and/or be received by the plurality of valleys (e.g., the first plurality of valleys 104) of the at least one connecting structure (e.g., the first connecting structure 100), and the plurality of ridges (e.g., the first plurality of ridges 102) of the at least one connecting structure (e.g., the first connecting structure 100) may be configured to engage with and/or be received by the plurality of valleys 314 of the accessory connecting structure 310. In some embodiments, the accessory connecting structure 310 may be engageable with the at least one connecting structure (e.g., the first connecting structure 100) using a male-to-male engagement. When the accessory connecting structure 310 is engaged with the connecting structure 100 of the handle 22 of the medical device 20, the side surfaces of the ridges 312 of the accessory connecting structure 310 may frictionally engage and press against the juxtaposed side surfaces of the ridges 102 of the connecting structure 100 of the handle 22.

In some embodiments, the accessory device 300 may be configured to be oriented with flattened body 302 substantially transverse to and without intersecting the central longitudinal axis of the medical device 20, the handle 22, and/or the elongate shaft 30 when the accessory connecting structure 310 is engaged with the at least one connecting structure (e.g., the first connecting structure 100, the second connecting structure 110, the third connecting structure 120, and/or the fourth connecting structure 130).

Additionally, in at least some embodiments, the accessory connecting structure 310 may be releasably engageable with the at least one connecting structure (e.g., the first connecting structure 100, the second connecting structure 110, the third connecting structure 120, and/or the fourth connecting structure 130) without the use of fasteners (e.g., screws, pins, clips, etc.). In some embodiments, the accessory connecting structure 310 may be releasably engageable with the at least one connecting structure (e.g., the first connecting structure 100, the second connecting structure 110, the third connecting structure 120, and/or the fourth connecting structure 130) without the use of latches. In some embodiments, the accessory connecting structure 310 may be releasably engageable with the at least one connecting structure (e.g., the first connecting structure 100, the second connecting structure 110, the third connecting structure 120, and/or the fourth connecting structure 130) without the use of tools.

Figure 11:
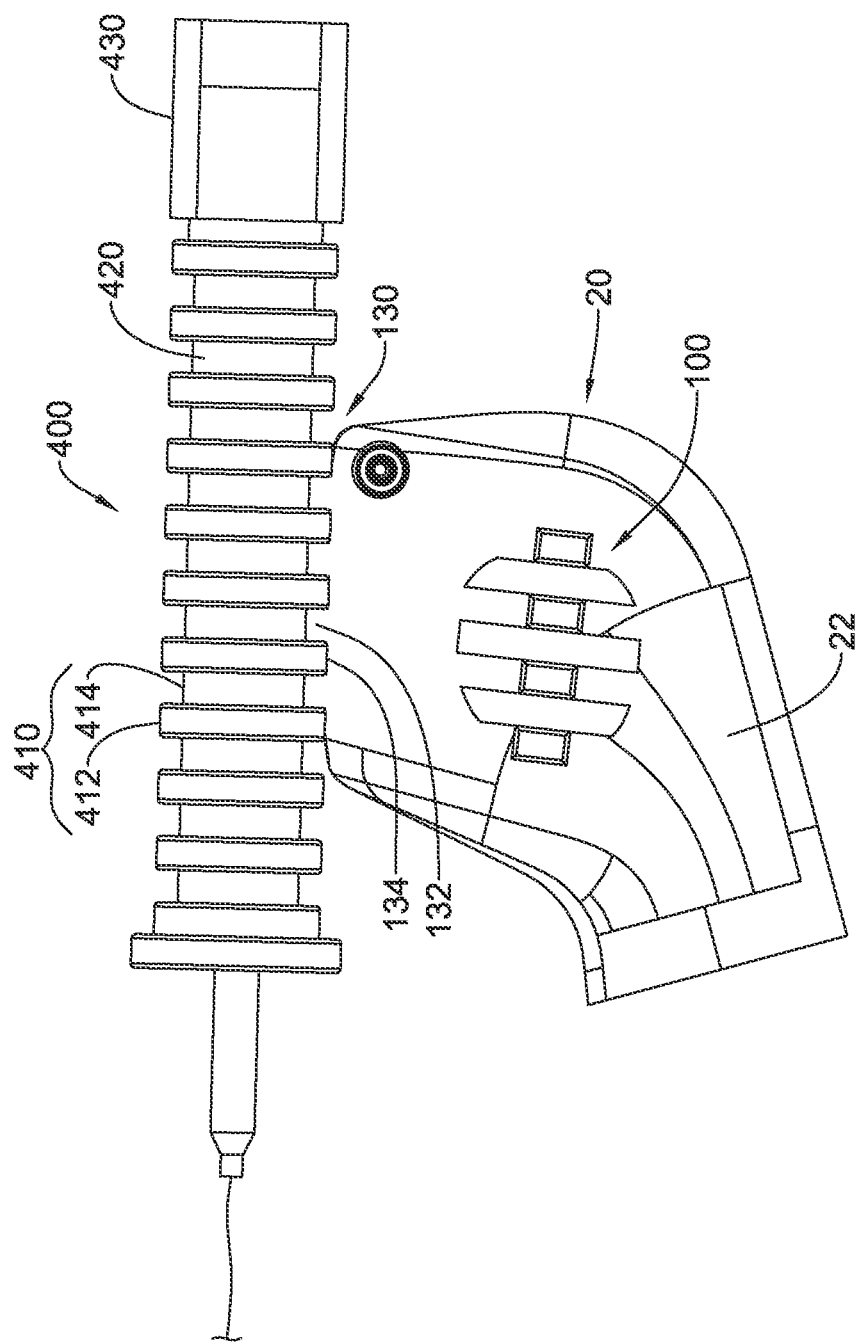
FIG. 11 illustrates engagement of the accessory device of FIG. 8 with the medical device of FIGS. 1-5.

FIG. 11 illustrates engagement of the accessory device 400 with a portion of the handle 22 of the medical device 20. As may be seen in the figures, the at least one connecting structure of the medical device 20 may be configured to engage with the accessory connecting structure 410 formed on the outer surface of the accessory device 400. Illustratively, FIG. 11 illustrates engagement of the accessory device 400 with the fourth connecting structure 130 formed on the outer surface of the medical device 20 and/or the handle 22. As will be appreciated, the accessory device 400 and/or the accessory connecting structure 410 may be engageable with the first connecting structure 100, the second connecting structure 110 (not shown), the third connecting structure 120 (not shown), and/or the fourth connecting structure 130. In the interest of brevity, the accessory device 400 and/or the accessory connecting structure 410 is shown engaging the fourth connecting structure 130 of the handle 22 of the medical device 20 and is described accordingly.

In some embodiments, the at least one connecting structure of the medical device 20 may be configured to engage with the accessory connecting structure 410 via an interference fit, a press fit, a friction fit, and the like, as seen in FIG. 11. Other means of engagement are also contemplated. The plurality of ridges 412 of the accessory connecting structure 410 may be configured to engage with and/or be received by the plurality of valleys (e.g., the fourth plurality of valleys 134) of the at least one connecting structure (e.g., the fourth connecting structure 130), and the plurality of ridges (e.g., the fourth plurality of ridges 132) of the at least one connecting structure (e.g., the fourth connecting structure 130) may be configured to engage with and/or be received by the plurality of valleys 414 of the accessory connecting structure 410. In some embodiments, the accessory connecting structure 410 may be engageable with the at least one connecting structure (e.g., the fourth connecting structure 130) using a male-to-male engagement. When the accessory connecting structure 410 is engaged with the connecting structure 130 of the handle 22 of the medical device 20, the side surfaces of the ridges 412 of the accessory connecting structure 410 may frictionally engage and press against the juxtaposed side surfaces of the ridges 132 of the connecting structure 130 of the handle 22.

In some embodiments, the accessory device 400 may be configured to be oriented with a central longitudinal axis substantially parallel to the central longitudinal axis of the medical device 20, the handle 22, and/or the elongate shaft 30 when the accessory connecting structure 410 is engaged with the at least one connecting structure (e.g., the first connecting structure 100, the second connecting structure 110, the third connecting structure 120, and/or the fourth connecting structure 130).

Additionally, in at least some embodiments, the accessory connecting structure 410 may be releasably engageable with the at least one connecting structure (e.g., the first connecting structure 100, the second connecting structure 110, the third connecting structure 120, and/or the fourth connecting structure 130) without the use of fasteners (e.g., screws, pins, clips, etc.). In some embodiments, the accessory connecting structure 410 may be releasably engageable with the at least one connecting structure (e.g., the first connecting structure 100, the second connecting structure 110, the third connecting structure 120, and/or the fourth connecting structure 130) without the use of latches. In some embodiments, the accessory connecting structure 410 may be releasably engageable with the at least one connecting structure (e.g., the first connecting structure 100, the second connecting structure 110, the third connecting structure 120, and/or the fourth connecting structure 130) without the use of tools.

The materials that can be used for the various components of the system(s) and the various elements thereof disclosed herein may include those commonly associated with medical devices. For simplicity purposes, the following discussion refers to the system. However, this is not intended to limit the devices and methods described herein, as the discussion may be applied to other elements, members, components, or devices disclosed herein, such as, but not limited to, the fluid management system, the medical device, the handle, the elongate shaft, the accessory device, the inflow pump, the fluid warming system, the controller, the supply line(s), the workstation, the display screen(s), etc. and/or elements or components thereof.

In some embodiments, the system, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, Elast-Eon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the system, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MM) compatibility is imparted into the system and/or other elements disclosed herein. For example, the system, and/or components or portions thereof, may be made of a material that does not substantially distort the image and create substantial artifacts (i.e., gaps in the image). Certain ferromagnetic materials, for example, may not be suitable because they may create artifacts in an MRI image. The system, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the system and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, poly methyl acetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical accessory mounting system, comprising:
 a medical device having a handle and an elongate shaft extending distally from the handle;
 wherein the handle includes at least one connecting structure formed in an outer surface of the handle, the at least one connecting structure comprising a plurality of ridges, wherein each of the plurality of ridges extends directly outward from and away from the outer surface of the handle;
 wherein the at least one connecting structure is configured to engage with an accessory connecting structure formed on an outer surface of an accessory device wherein the accessory connecting structure is engageable with the at least one connecting structure using a male-to-male engagement in which side surfaces of the plurality of ridges of the at least one connecting structure frictionally engage side surfaces of a plurality of ridges disposed on the accessory connecting structure.

2. The medical accessory mounting system of claim 1, wherein the at least one connecting structure further comprises a plurality of valleys, each valley being disposed between adjacent ridges of the plurality of ridges, wherein the at least one connecting structure is configured to engage with the accessory connecting structure such that at least two of the plurality of valleys are engaged with the accessory connecting structure.

3. The medical accessory mounting system of claim 1, wherein the plurality of ridges are oriented parallel to each other and each of the plurality of ridges extends in a direction transverse to a longitudinal axis of the handle.

4. The medical accessory mounting system of claim 1, wherein the accessory connecting structure is releasably engageable with the at least one connecting structure without the use of additional fasteners.

5. The medical accessory mounting system of claim 1, wherein the accessory connecting structure is releasably engageable with the at least one connecting structure without the use of latches.

6. The medical accessory mounting system of claim 1, wherein the accessory connecting structure is releasably engageable with the at least one connecting structure without the use of tools.

7. The medical accessory mounting system of claim 1, wherein the at least one connecting structure includes a first connecting structure and a second connecting structure, wherein an entirety of the first connecting structure is spaced apart from the second connecting structure along the outer surface of the handle.

8. The medical accessory mounting system of claim 7, wherein the accessory connecting structure is engageable with the first connecting structure and the second connecting structure.

9. The medical accessory mounting system of claim 1, wherein the accessory connecting structure comprises a plurality of ridges and a plurality of valleys.

10. The medical accessory mounting system of claim 1, wherein the plurality of ridges of the at least one connecting structure are monolithically formed with the outer surface of the handle.

11. The medical accessory mounting system of claim 1, wherein the plurality of ridges of the at least one connecting structure are spaced apart from each other by a plurality of valleys, wherein the plurality of ridges are oriented parallel to one another, and wherein a plurality of ridges of the accessory connecting structure are simultaneously engageable in the plurality of valleys of the at least one connecting structure to connect the accessory device to the handle.

12. An endoscopic system, comprising:
 an endoscope having a handle and an elongate shaft extending distally from the handle; and
 an endoscopic accessory device;
 wherein the handle includes at least one connecting structure formed in an outer surface of the handle, the at least one connecting structure comprising a plurality of ridges alternating with a plurality of valleys;
 wherein the at least one connecting structure is configured to engage with an accessory connecting structure formed on an outer surface of the endoscopic accessory device such that at least two of the plurality of ridges and at least two of the plurality of valleys are engaged with the accessory connecting structure.

13. The endoscopic system of claim 12, wherein the at least one connecting structure includes a first connecting structure and a second connecting structure spaced apart from the first connecting structure.

14. The endoscopic system of claim 13, wherein the at least one connecting structure includes a third connecting structure spaced apart from the first connecting structure and the second connecting structure.

15. The endoscopic system of claim 12, wherein the accessory connecting structure is engageable with the at least one connecting structure using a male-to-male engagement in which side surfaces of the plurality of ridges of the at least one connecting structure frictionally engage side surfaces of a plurality of ridges disposed on the accessory connecting structure.

16. The endoscopic system of claim 12, wherein each of the plurality of ridges extends directly from the outer surface of the handle and is oriented transverse to a longitudinal axis of the handle.

17. The endoscopic system of claim 16, wherein adjacent ridges of the plurality of ridges are spaced apart from each other by one of the plurality of valleys, each of the ridges and valleys being oriented parallel to each other.

18. The medical accessory mounting system of claim 10, wherein the plurality of ridges of the at least one connecting structure are molded as part of the handle.

\* \* \* \* \*